United States Patent
Erickson et al.

(10) Patent No.: US 9,821,314 B2
(45) Date of Patent: Nov. 21, 2017

(54) METHODS, SYSTEMS, AND APPLICATIONS FOR SOLAR-THERMAL MICROFLUIDIC PCR

(71) Applicant: CORNELL UNIVERSITY, Ithaca, NY (US)

(72) Inventors: David Erickson, Ithaca, NY (US); Li Jiang, Ithaca, NY (US); Matthew Mancuso, Bohemia, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 149 days.

(21) Appl. No.: 14/429,407

(22) PCT Filed: Sep. 18, 2013

(86) PCT No.: PCT/US2013/060343
§ 371 (c)(1),
(2) Date: Mar. 19, 2015

(87) PCT Pub. No.: WO2014/047137
PCT Pub. Date: Mar. 27, 2014

(65) Prior Publication Data
US 2015/0238967 A1    Aug. 27, 2015

Related U.S. Application Data

(60) Provisional application No. 61/704,732, filed on Sep. 24, 2012.

(51) Int. Cl.
*C12Q 1/68* (2006.01)
*C12P 19/34* (2006.01)
(Continued)

(52) U.S. Cl.
CPC ............... *B01L 7/52* (2013.01); *B01L 3/5027* (2013.01); *B01L 7/5255* (2013.01); *C12Q 1/686* (2013.01);
(Continued)

(58) Field of Classification Search
None
See application file for complete search history.

(56) References Cited

U.S. PATENT DOCUMENTS 5,558,947 A    9/1996  Robison
6,127,061 A    10/2000 Shun et al.
(Continued)

FOREIGN PATENT DOCUMENTS

WO    9960654 A1      11/1999
WO    2013077870 A1   5/2013

OTHER PUBLICATIONS

Snodgrass et al., "KS-Detect—Validation of Solar Thermal PCR for the Diagnosis of Kaposi's Sarcoma Using Pseudo-Biopsy Samples," PLoS One, 2016, vol. 11, No. 1, pp. 1-15.*
(Continued)

*Primary Examiner* — Young J Kim
(74) *Attorney, Agent, or Firm* — Bond, Schoeneck & King, PLLC; William Greener; Erin Phillips

(57) ABSTRACT

Disclosed are methods and apparatus for solar-thermal microfluidic polymerase chain reaction. A device comprises a microfluidic chip including at least one PCR region, an energy absorption layer disposed adjacent to the microfluidic chip, a solar energy concentrator adapted to produce a plurality of temperature profiles on the microfluidic chip adapted to facilitate PCR, and a photomask disposed between the solar energy concentrator and the microfluidic chip.

20 Claims, 8 Drawing Sheets

(51) Int. Cl.
*B01L 7/00* (2006.01)
*G01N 35/00* (2006.01)
*B01L 3/00* (2006.01)

(52) U.S. Cl.
CPC . *B01L 3/502715* (2013.01); *B01L 2300/0803* (2013.01); *B01L 2300/0816* (2013.01); *B01L 2300/12* (2013.01); *B01L 2300/168* (2013.01); *B01L 2300/1861* (2013.01); *G01N 2035/00158* (2013.01)

(56) References Cited

U.S. PATENT DOCUMENTS

| | | | |
|---|---|---|---|
| 6,734,436 | B2 | 5/2004 | Faris et al. |
| 8,309,260 | B2 | 11/2012 | Moore |
| 2009/0078326 | A1 | 3/2009 | Rosario et al. |
| 2010/0151336 | A1 | 6/2010 | Nakanishi |
| 2011/0027664 | A1 | 2/2011 | Burchardt et al. |
| 2012/0021303 | A1 | 1/2012 | Amendola et al. |
| 2012/0270116 | A1 | 10/2012 | Cho et al. |
| 2013/0011754 | A1 | 1/2013 | Tanaami et al. |
| 2013/0115528 | A1 | 5/2013 | Lu |
| 2013/0143132 | A1 | 6/2013 | Mizuno |
| 2013/0157149 | A1 | 6/2013 | Peled et al. |
| 2013/0164638 | A1 | 6/2013 | Tanaami et al. |
| 2013/0183591 | A1 | 7/2013 | Dickson |

OTHER PUBLICATIONS

International Search Report and Written Opinion Form PCT/ISA/220, International Application No. PCT/US2013/060343, p. 1-11, International Filing date Sep. 18, 2013.

Park et al., Advances in Microfluidic PCR for Point-Of-Care Infectious Disease Diagnostics, Biotechnology Advances, Nov. 2011, vol. 29. pp. 830-839.

Chen et al., Optofluidic Opportunities in Global Health, Food, Water and Energy, Nanoscale, Epub Jun. 13, 2012, vol. 4, pp. 4839-4857.

Li et al., On-Chip Integrated Multi-Thermo-Actuated Microvalves of Poly(N-Isopropylacrylamide) for Microflow Injection Analysis, Analytica Chimica Acta, 2010, vol. 665, pp. 107-112.

Hartmann et al., A Rechargeable Room-Temperature Sodium Superoxide (Nao2) Battery, Nature Materials, 2013, vol. 12, pp. 228-232.

Lee et al., Metal—Air Batteries With High Energy Density: Li—Air versus Zn—Air, Advanced Energy Materials, Jan. 1, 2011, vol. 1, Issue 1, pp. 34-50, http://onlinelibrary.wiley.com/doi/10.1002/aenm.201000010/epdf.

Cheng et al., Metal—Air Batteries: From Oxygen Reduction Electrochemistry to Cathode Catalysts, 2012, Chemical Society Reviews, Issue 6, http://pubs.rsc.org/en/content/articlelanding/2012/cs/c1cs15228a#!divAbstract.

* cited by examiner

METHODS, SYSTEMS, AND APPLICATIONS FOR SOLAR-THERMAL MICROFLUIDIC PCR

CROSS-REFERENCE TO RELATED APPLICATIONS

This application claims priority to U.S. Provisional Patent Application Ser. No. 61/704,732, filed on Sep. 24, 2012 and entitled "Solar Powered PCR Apparatus, Methods, and Applications," the entire disclosure of which is incorporated herein by reference.

STATEMENT OF GOVERNMENT INTEREST

The work leading to the present invention was supported in part by the National Science Foundation under CAREER award grant number CBET-0846489. The United States Government has certain rights in the invention.

BACKGROUND

The present invention relates to methods, devices, and applications pertaining to point of care diagnostics and, more specifically, to methods and apparatuses for solar-thermal microfluidic polymerase chain reaction ("PCR") for point-of-care diagnostics.

Over the past few years, point-of-care diagnostics and analysis has become increasingly necessary. Utilizing this technology, samples are obtained and analyzed at the patient's bedside, including in hospitals, outpatient care centers, homes, and even in the field locations where other options do not exist.

Although point-of-care diagnostics and analysis pose a number of challenges, some work has recently been performed to address some of these challenges. For example, point-of-care devices have been developed using mechanical, electrical, and optical techniques to analyze samples quickly utilizing only minute quantities. Yet for all of the successes of these devices, a number of limitations still exist including the need to pre-process samples, the ability to work in a range of buffers (including those used to lyse cells), high sensitivity limits, and often a limited ability to detect multiple targets.

One type of point-of-care device is a PCR machine. PCR is a well-known and frequently-used technology that amplifies copies of DNA across several orders of magnitude. This is especially useful for accurately diagnosing diseases in which the concentration of target DNA in a sample is extremely low. Many works have demonstrated the integration of PCR into microfluidic devices with the goal of applying it to point-of-care diagnostics. Unfortunately, one of the fundamental limitations across all technologies is the amount of energy required to perform the high-temperature thermal cycling (from 65° C. to 95° C.), which significantly restricts the number of runs available per battery. Further, most PCR devices require electrical heaters, actuators, controllers, and other components, all of which significantly increase the energy needs and overall costs of the device.

Accordingly, there is a continued demand for a point-of-care PCR technology that addresses the many limitations that exist in current devices and methods.

BRIEF SUMMARY

Systems and methods for solar-thermal microfluidic PCR. According to an aspect, a solar-thermal microfluidic PCR device comprises: (i) a microfluidic chip including at least one PCR region; (ii) an energy absorption layer disposed adjacent to the microfluidic chip; (iii) a solar energy concentrator adapted to produce a plurality of spatially modulated temperature profiles on the microfluidic chip, the plurality of spatially modulated temperature profiles adapted to facilitate PCR within the PCR region; and (iv) a photomask disposed between the solar energy concentrator and the microfluidic chip. The photomask can be adjustable. For example, according to one aspect the opacity of the photomask is adjustable.

According to an aspect, the device further comprises a sensor such as a thermometer coupled to the microfluidic device, and a user interface coupled to the sensor.

According to yet another aspect, the distance between the solar energy concentrator and the microfluidic device is adjustable.

According to one aspect, the photomask comprises a plurality of nested aluminum rings.

According to an aspect, the plurality of spatially modulated temperature profiles comprises a first, denaturation temperature profile, a second, annealing temperature profile, and a third, elongation temperature profile. According to yet another aspect, the microfluidic chamber is configured to allow the sample to pass through the three temperature profiles in a time ratio of approximately 4:4:9.

According to an aspect is a system for solar-thermal microfluidic polymerase chain reaction (PCR) amplification of nucleic acid, the system comprising: (i) a sample comprising nucleic acid; and (ii) a solar-thermal microfluidic PCR device comprising: (i) a microfluidic chip comprising a microfluidic chamber adapted to facilitate PCR of the sample; (ii) an energy absorption layer disposed adjacent to the microfluidic chip; and (iii) a solar energy concentrator coupled to the energy absorption layer and adapted to produce a plurality of spatially modulated temperature profiles on the microfluidic chip, the plurality of spatially modulated temperature profiles adapted to facilitate PCR within the PCR region; and (iv) a photomask disposed between the solar energy concentrator and the microfluidic chip.

According to an aspect, the device further comprises a thermometer.

According to another aspect, the opacity of the photomask disposed between the solar energy concentrator and the microfluidic chip is adjustable.

According to yet another aspect, the plurality of spatially modulated temperature profiles comprises a first, denaturation temperature profile, a second, annealing temperature profile, and a third, elongation temperature profile.

According to an aspect is a method for facilitating microfluidic polymerase chain reaction (PCR) amplification of nucleic acid, the method comprising the steps of: providing a sample comprising nucleic acid; providing a solar-thermal microfluidic PCR device comprising: (i) a microfluidic chip comprising a microfluidic chamber adapted to facilitate PCR of the sample; (ii) an energy absorption layer disposed adjacent to the microfluidic chip; (iii) a solar energy concentrator adapted to produce a plurality of spatially modulated temperature profiles on the microfluidic chip, the plurality of spatially modulated temperature profiles adapted to facilitate PCR within the PCR region; and (iv) a photomask disposed between the solar energy concentrator and the microfluidic chip; and applying the sample to the microfluidic chamber; and performing PCR using the solar-thermal microfluidic PCR device.

According to an aspect, further comprising the step of detecting a temperature of the solar-thermal microfluidic PCR device.

According to another aspect, the method further comprises the step of adjusting the opacity of the photomask.

According to yet another aspect, the method further comprises the step of adjusting the distance between the solar energy concentrator and the microfluidic device is adjustable.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 7:
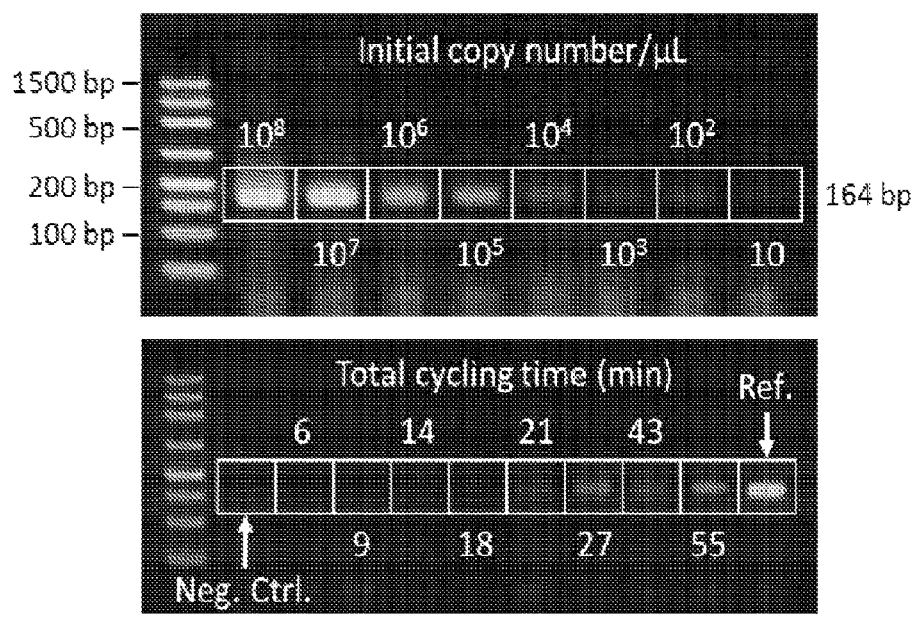
Figure 8:
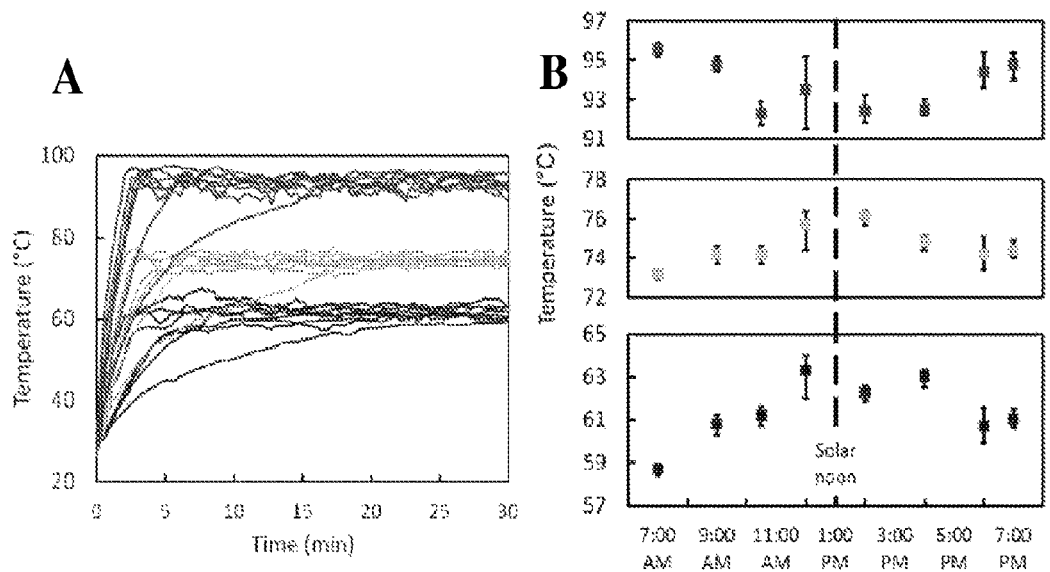
Figure 9:
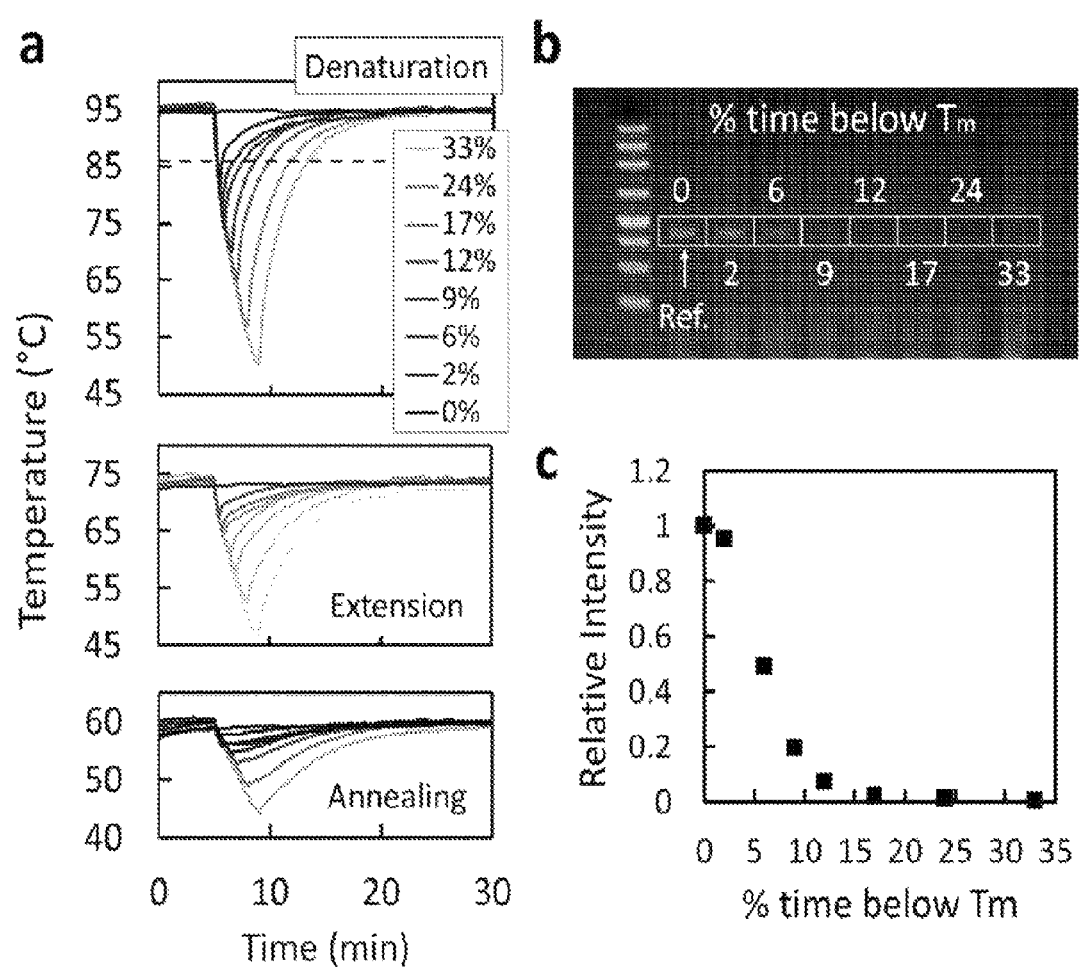
Figure 10:
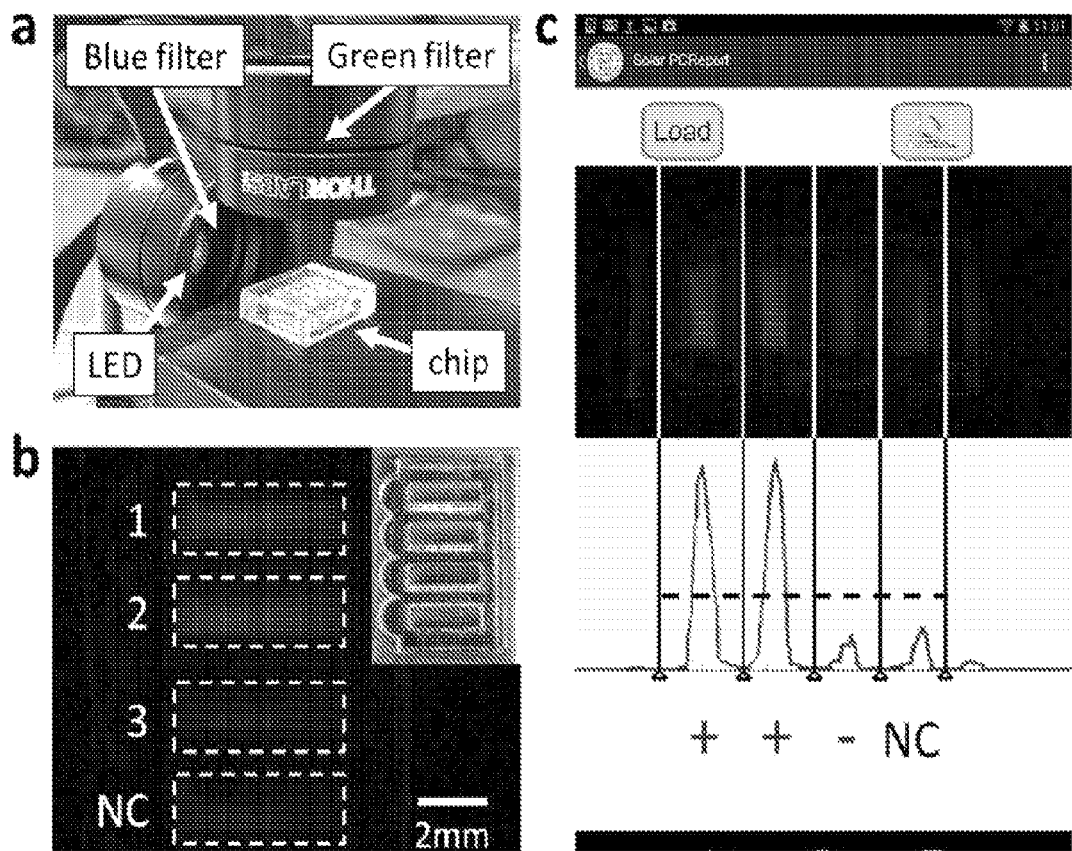

FIG. 6(A) is a graph of a simulation showing plateaued temperature profiles at the plane of the microchannel according to an embodiment, and FIG. 6(B) is a graph of measurements in (i) April and (ii) May in the central New York state town of Ithaca demonstrating the ability of the device to achieve similar on-chip temperatures using the same mask, and (iii) simulations providing thermal profiles from 0° C. to 30° C. ambient temperature, according to an embodiment;

FIG. 7 is an image of an electrophoresis analysis of amplicon produced according to an embodiment of methods described herein;

FIG. 8 are graphs of (A) thermal measurements from 7 AM to 7 PM showing relatively consistent values, and (B) averaged temperature data showing day-long trends, according to an embodiment;

FIG. 9 is (a) graphs of simulated temperature variation for denaturation, extension and annealing due to blocking of the light, where simulated clouding times ranged from 0 s (darkest curve) to 4 min (lightest curve); and (b) images of gel electrophoresis and (c) corresponding band measurements show diminishing intensities as a function of the duration of simulated cloud coverage; and FIG. 10 is (a) a fluorescence detection setup includes a blue filter between the LED and the chip and a green filter between the chip and the camera; (b) PDMS chip (inset) containing 4 tests: solar thermal PCR performed using KSHV+ samples (1, 2) and a KSHV-sample (3) and traditional PCR using negative control (NC); and (c) a screenshot of a smartphone application that analyzes the fluorescence signals, showing high intensities for samples 1 and 2 and low intensities for sample 3 and NC, according to an embodiment.

DETAILED DESCRIPTION

According to an embodiment are methods for employing solar energy to produce spatially modulated thermal patterns that facilitate on-chip PCR. Sunlight is concentrated through a lens and passed through a photomask to create a specific intensity profile on the chip. An absorber layer made from carbon black converts the light into a thermal pattern designed to match the denaturation, annealing, and elongation stages of a traditional PCR. According to an embodiment, the microfluidic channel is specifically designed such that a sample passes through each of the temperature zones for a predetermined time, thus amplifying the target.

According to an embodiment, the device comprises a glass lens and a movable PCR chip. The focused sunlight passes through a ring-shaped mask and is converted into heat by an absorber layer. Due to the masking of light in specific regions, three temperature zones at 95° C. (denaturation), 72° C. (extension) and 60° C. (annealing) are created along the radius of the chip. A microfluidic channel then repeatedly guides a sample through these three zones for a predetermined number of cycles. The channel geometry dictates a predetermined residence time ratio (denaturation to extension to annealing), effectively creating the thermal conditions that induce PCR. This microfluidic technique is known as continuous-flow PCR and exhibits fast reaction speeds, minimal cross-contamination, high throughput, and facilitates microfluidic device integration, making it highly attractive for many different applications.

Figure 6:
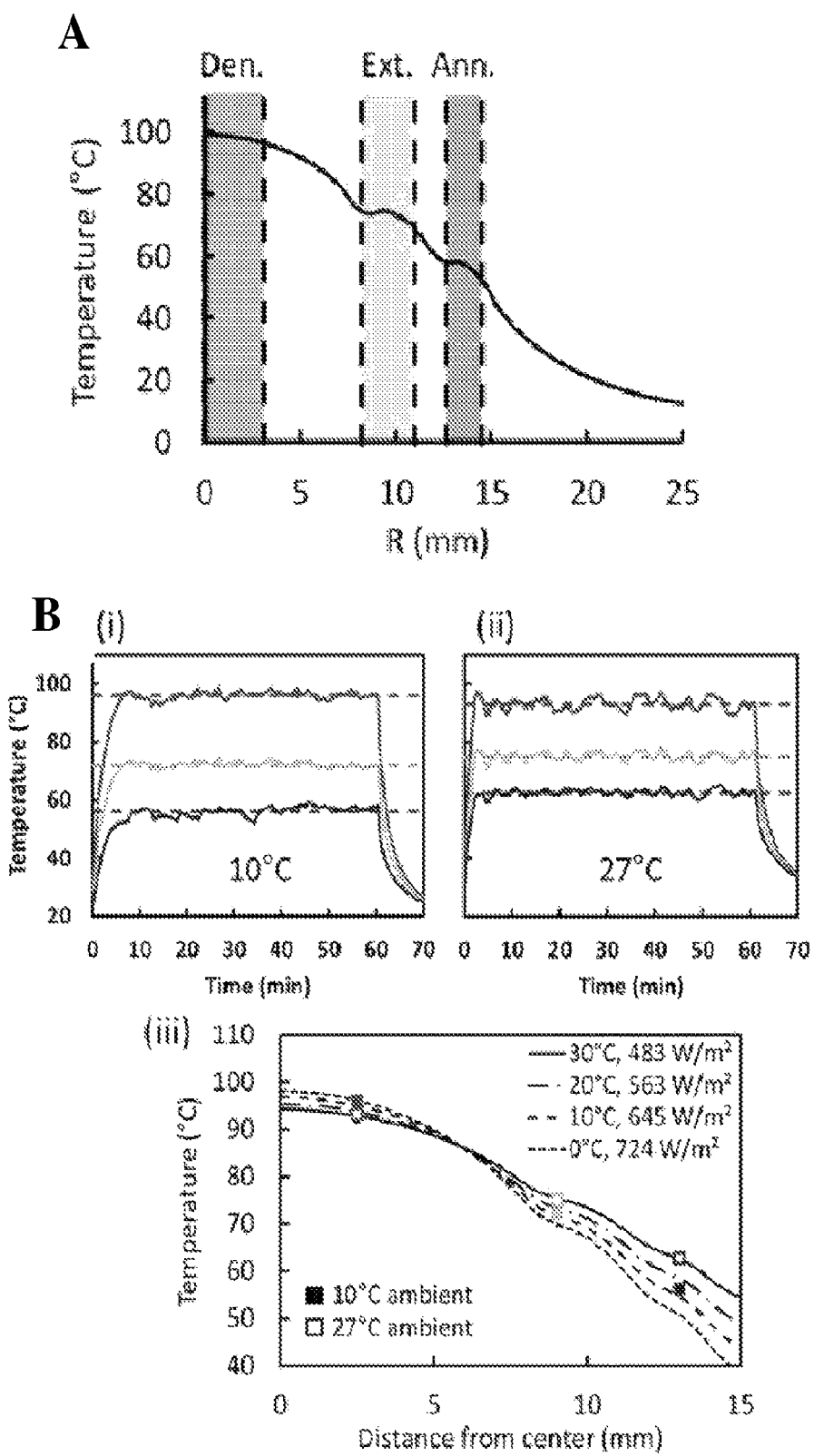

According to another embodiment, the masking rings can be designed such that the thermal profile generated by the masked light exhibits plateaus at or near 95° C., 72° C., and 60° C. for a given solar intensity and ambient temperature (FIG. 6). For example, FIG. 6(B) shows temperatures obtained in April (10° C. ambient) and May (27° C. ambient) of 2013 in Ithaca, New York using the same mask. For these measurements, the lens-to-chip distance was first set to 85 mm to quickly heat the chip. Once temperatures near PCR requirements were reached, the distance was reduced to 79 mm in April or 68 mm in May. Through this process, on-chip temperature changes were minimized to 3° C. for denaturation and extension and 6° C. for annealing. Simulations suggest that over the range of 0° C. to 30° C. roughly 75% to 50% of peak insolation (1000 W/m$^2$) is sufficient for PCR (FIG. 6(B)(iii)).

According to another embodiment is a radial design for the solar-thermal PCR device, as depicted in FIG. 3. This design offers the same temperature along the azimuthal direction, allowing all cycles to run optimally under a uniform light source such as sunlight. Additionally, the lens and the microfluidics are separated, allowing for easy replacement of the microfluidic cartridge. To account for variations in solar intensity, the center of the chip can have an embedded thermocouple which is read via the analog port of a smartphone and interpreted by a simple application or separate software program. According to one embodiment, the operator must simply adjust the height of the lens prior to starting the flow to ensure the proper temperature distribution across the chip during the assay, as shown in FIG. 3. This changes the intensity of the sunlight absorbed by the chip, which compensates for different ambient temperatures and allows the system to function under a range of conditions.

The microfluidic component of the device can be any microfluidic device, channel, or component suitable for manipulating a sample, including but not limited to lab-on-a-chip and similar microfluidic designs. According to an embodiment, the microfluidic device is a commercially-available microfluidic chip. According to another embodiment, the microfluidic device is designed and manufactured specifically for the solar-thermal device.

Compared to traditional thermal cycling in which the machine cycles through the three different temperatures while keeping the sample stationary, continuous-flow PCR carries the benefit of enabling faster reaction times but has the disadvantage of requiring more energy per cycle. Therefore, commercially available kits perform PCR in the traditional manner in order to maximize their operational lifetime before needing to recharge the battery. However, when utilizing solar energy for heating the amount of energy required by the system is no longer a technical limitation. Therefore, by implementing a continuous-flow paradigm, there is the advantage of potentially faster reaction times without sacrificing the duration of the device's usage. Further, the solar-thermal PCR device eliminates the major energy consuming portion of a PCR assay through the use of sunlight to heat the system. This removes the need for a battery pack and battery charger, making the device less expensive and lighter in weight than commercially available kits.

According to an embodiment, the device comprises one or more thermocouples. For example, the device can comprise three thermocouples in the chip or otherwise placed in the device and connected by a microcontroller to a smartphone, transceiver, or other computerized device. Further, the device and or associated system can comprise a smartphone application or other computer program that measures the on-chip temperatures throughout the test. Indeed, a microcontroller can relay electrical signals between the one or more thermocouples and a smartphone application or other computer program that interprets those signals as temperatures. According to one embodiment, the thermocouples can be imbedded in or otherwise associated with the chip so that the user can read the on-chip temperatures.

According to another embodiment, the device or system can further comprise a fluorescence detector for detecting the PCR-amplified target. Once the DNA sample has been amplified, it is mixed with a DNA-specific dye that fluoresces green when excited with blue light in the presence of double stranded DNA. Other color combinations are possible. An apparatus powered by a smartphone will excite the sample and detect the fluorescent signal to provide on-site diagnostics.

According to yet another embodiment, the device can comprise rotational and/or tilting abilities or functionality. Either a portion of the device, or the entire device, can rotate or tilt. For example, the angle of the sun hitting the device depends upon a variety of factors such as the time of year and the latitude of the device. Accordingly, the device can comprise a hinge or tilting stage that points the lens towards the sun in order to more completely capture the incoming solar radiation. According to another embodiment, the device can comprise an automated motor or mount, similar to a telescope motor, which keeps the device oriented toward the sunlight.

Figure 3A:
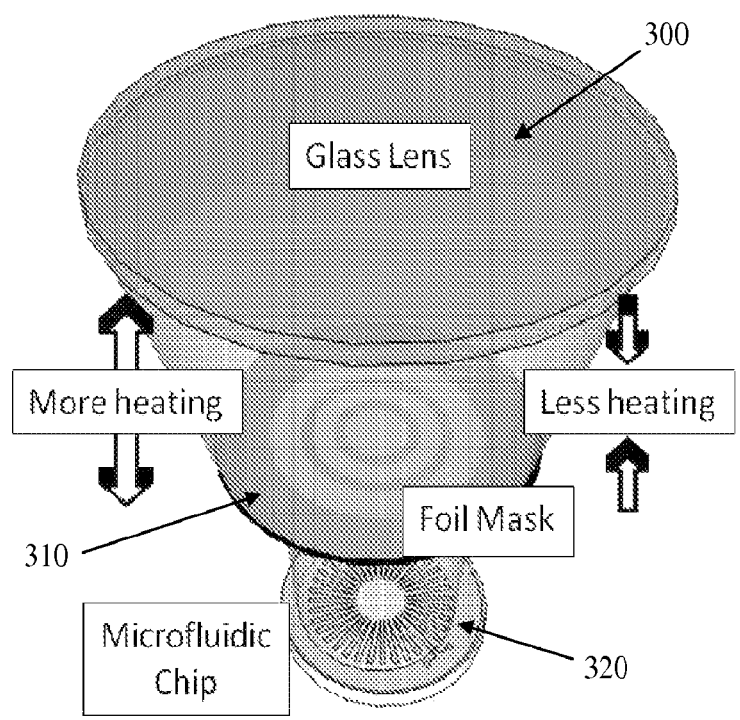
FIG. 3A is a diagrammatic representation of a glass lens according to an embodiment.

Referring now to the drawings, wherein like reference numerals refer to like parts throughout, there is seen in FIG. 3A a solar-thermal microfluidic PCR device according to one embodiment. The device includes a lens 300, photomask 310, and microfluidic device 320. Although a particular structure is shown in FIG. 3, many other formulations and structures are possible in order to maximize the detected light, to stabilize the temperature profiles, or for a variety of other requirements.

According to one embodiment, the solar-thermal PCR device is constructed from any of a variety of materials, including plastics, wood, and metal, among many others. Similarly, the one or more lenses can constructed from any of a variety of materials, including plastics and glass. For example, the one or more lenses may be constructed using polydimethylsiloxane ("PDMS"). According to one embodiment, the device comprises two lenses designed with specific curvatures such that a uniform light source incident on them is focused in the correct ratios on to the carbon black absorber layer to achieve temperatures needed for denaturation (95° C.) and elongation (72° C.) steps.

Figure 3B:
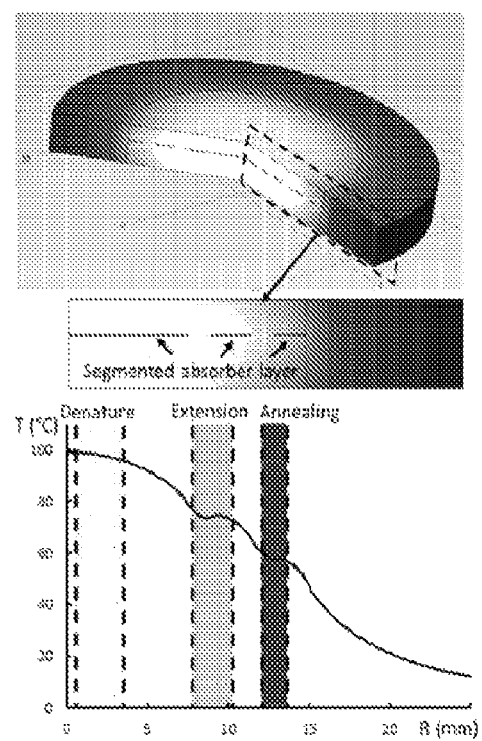
FIG. 3B is a diagrammatic representation of three aluminum foil rings forming a foil mask that results in three different temperature profiles, according to an embodiment.

According to another embodiment, the lens comprises glass or a similar material. The device can comprise a photomask situated between the glass lens and the microfluidic device, as shown in FIG. 3A. The photomask can be composed of a variety of materials, including three nested aluminum foil rings which form three different temperature profiles, as depicted in FIG. 3B.

Figure 4:
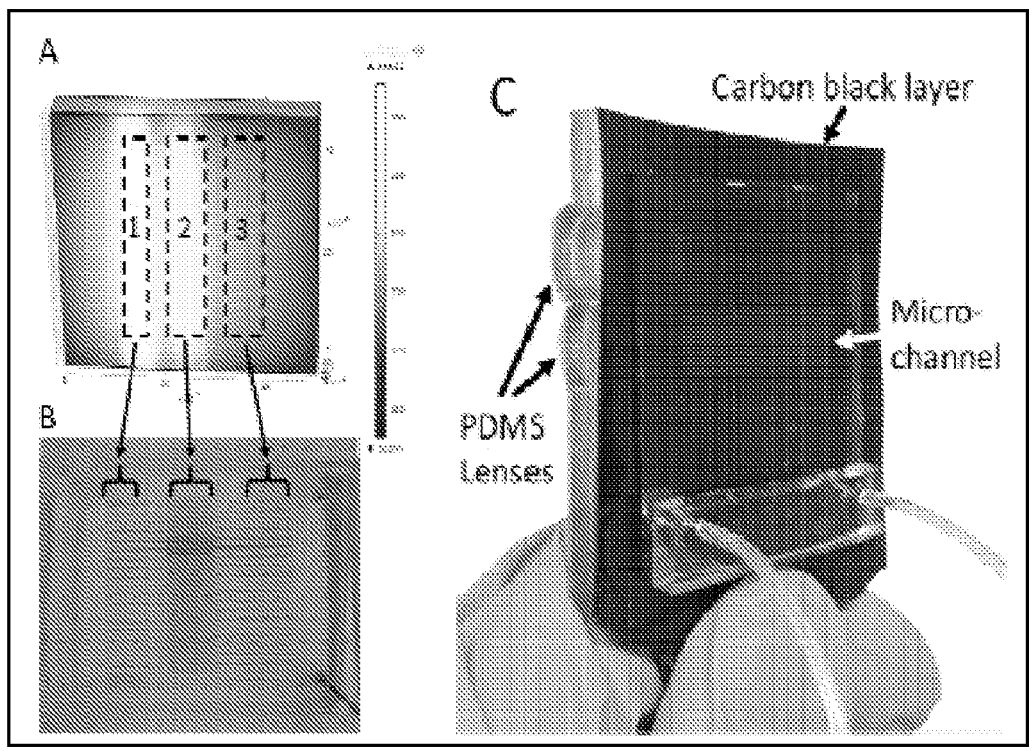
FIG. 4 is a schematic representation of a microfluidic device design according to an embodiment.

According to one embodiment, the device includes a microfluidic component with channel structure designed based on simulations to allow reagents to pass through 20-35 cycles of the denaturation, annealing and elongation steps, as depicted in FIG. 4. The microfluidic channel can be fabricated using a variety of methods, including but not limited to standard photolithography techniques. For example, the channel geometry is etched onto a chrome mask using a mask writer, which is then used to create an SU-8 mold on a silicon wafer. PDMS is poured over this, cured at 80° C. and lifted off to get the channel structure. This is then plasma bonded with a 100 μm thin film of cured PDMS to create a closed structure. Finally, the channel structure is reversibly bonded to the lens system, resulting in the embodiment of the device depicted in FIG. 4(c).

Figure 1:
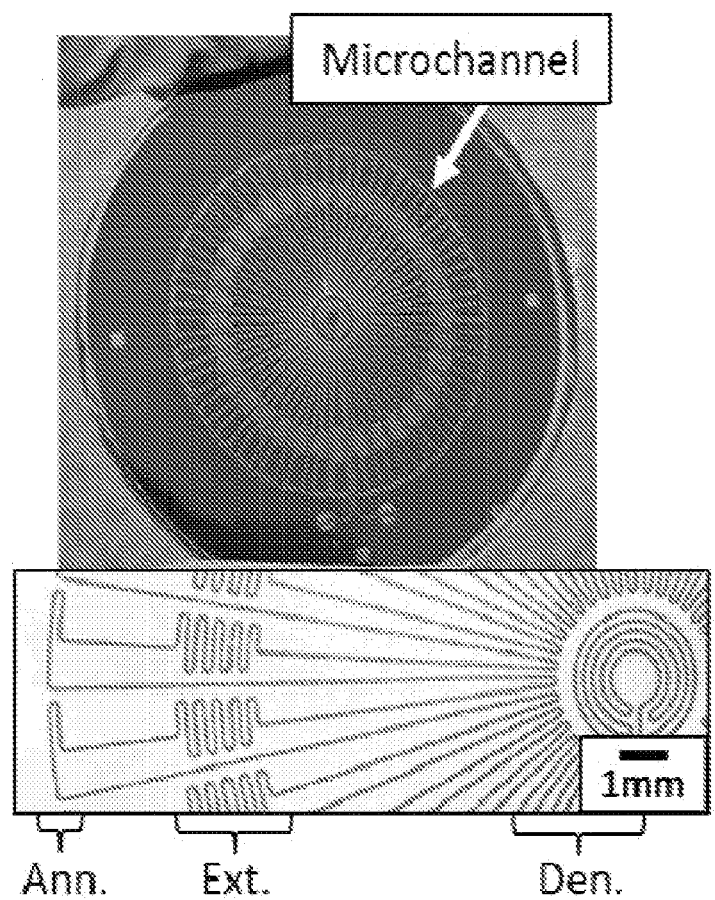
FIG. 1 is a schematic representation of a circular microfluidic chip with one embodiment of a heat pattern.
Figure 2A:
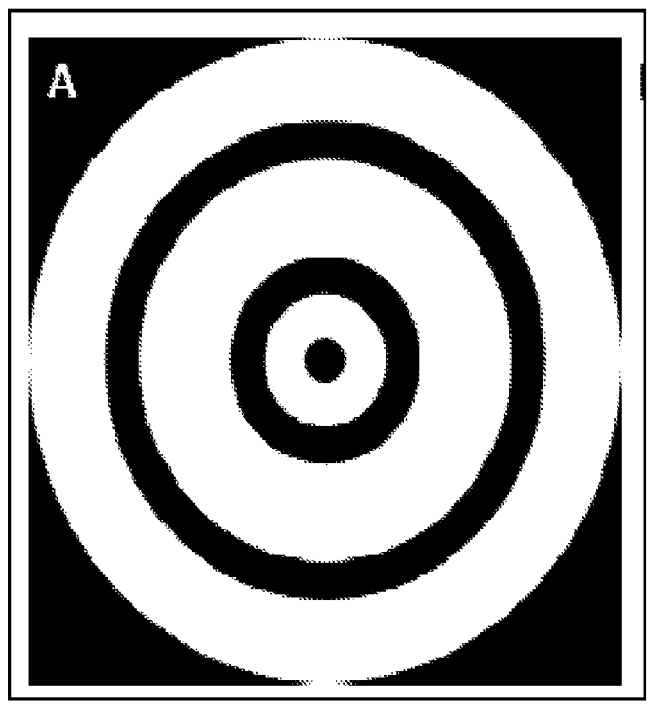
FIG. 2A is an example of a patterned photomask designed to regulate the temperature on a chip according to an embodiment.
Figure 2B:
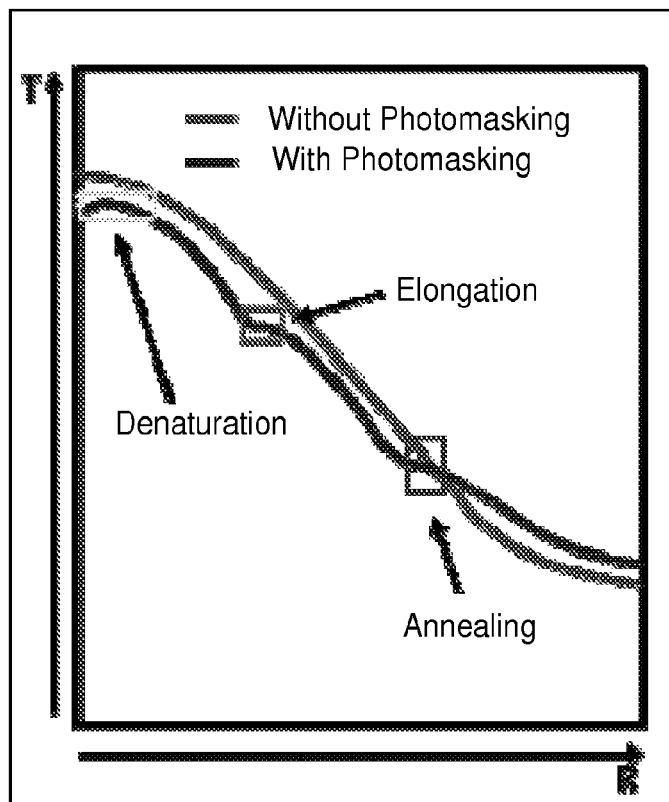
FIG. 2B is a graph of temperature profiles with and without a photomask, demonstrating that a photomask can create a temperature profile suitable for PCR.

According to one embodiment, the locations of the photomask and the microfluidic stage can be adjusted with respect to the lens to generate the correct temperature profile. To facilitate that, unique photomask patterns and absorber layer concentrations are utilized. As FIG. 2 depicts, without using a photomask the temperature profile would not by itself produce the three temperature zones required for PCR and an appropriate design of the microfluidic geometry would be needed to achieve proper cycling. Even then, it could be difficult to obtain the necessary temperature profile in a given region, as each step of PCR only operates optimally within a relatively narrow range of temperatures. According to yet another embodiment, a second option is to use a specific photomask that varies the amount of light energy that reaches the absorber layer. The photomask can be created from a variety of materials, including paper, plastic, metal, and a variety of other materials. According to one embodiment, the photomask is designed using software and printed onto transparency paper, although a wide variety of other methods are possible. For example, the photomask can be printed onto paper and then used to create a cutout of aluminum foil or other photomask material.

While the majority of the energy needed to run this device is for heating, according to one embodiment the system may also require real-time feedback of the temperatures on the chip. In one aspect of this technology, a smartphone application can be designed and utilized that can connect to one or several thermocouples to provide temperature readouts.

Based on this feedback, the photomask and microfluidic chip can be manually adjusted to get the correct temperatures. In other embodiments, the smartphone or portable computer (including but not limited to a tablet, PDA, smart watch, or other portable computerized device) can provide further functionality, including control of the positions of the stages, pumping of the sample fluid, and analysis of the processed sample.

EXAMPLE 1

According to one embodiment, the one or more lenses can comprise a flat region where light is not focused, which facilitates annealing at 65° C. Measurements of the temperatures at various locations were recorded and matched with a numerical simulation of the heat transfer in the device. The PDMS lens system was made by first designing the concave "negative" version of the lenses in AutoCAD to use as a mold. A laser cutter was used to make an acrylic glass template, for which PDMS base and curing agent in a ratio of 10:1 was poured over and baked at 80° C., resulting in the lens system. To fabricate the absorber layer, a mixture of carbon black, PDMS base and PDMS curing agent in a ratio of 0.01:1:0.1 was poured on the flat surface (opposite to the side with the lenses) and spun at 1400 RPM to create a film of about 50 µm in thickness.

EXAMPLE 2

Figure 5:
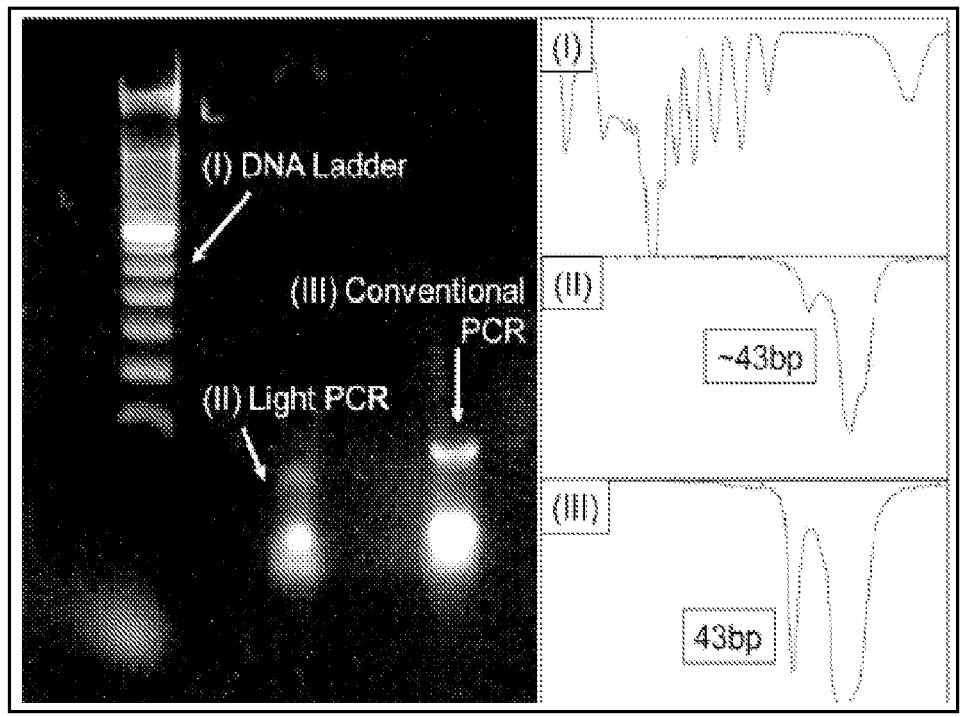
FIG. 5 is a figure of a gel electrophoresis depicting amplification of a 43 bp target utilizing solar-thermal PCR according to an embodiment.

To perform preliminary tests using an embodiment of the PCR device, a projector combined with a collimating lens was used as the light source to ensure a constant and uniform incident light. This embodiment was utilized to demonstrate amplification of a 43 bp segment of genomic DNA extracted from Kaposi's sarcoma herpes virus (KSHV), compared to conventional PCR, as shown in FIG. 5. As can be seen from the image, amplification is observed for light-powered PCR and conventional PCR. The rectangular design utilized for this embodiment might be limiting, as the temperature may not be constant along the length of the lenses. This could potentially prevent some of the cycles from operating optimally.

According to another embodiment, the device can comprise photovoltaic solar cells to power on-chip micro-heaters. However, one disadvantage of photovoltaic solar cells is the low efficiency of the solar-electric-thermal energy conversion process. For example, low-cost commercial photovoltaic cells are 15% efficient in converting incident photons to electricity whereas solar-thermal energy conversion is nearly 100% efficient since all photons incident on a broadband absorber are necessarily converted to heat.

EXAMPLE 3

According to one embodiment, the PCR chip was 50 mm in diameter and 5 mm in thickness and is comprised of three parts. The top part holds three thermocouples (Omega, 5TC-TT-K-36-36) placed immediately below the three aluminum foil rings. These are secured in place inside 2 mm of PDMS (10:1 ratio of base to curing agent). The bottom piece contains the absorber layer and the microfluidic channel. The absorber is a mixture of carbon black, PDMS base and PDMS curing agent in a 0.01:1:0.05 weight ratio. This is spin-coated onto a 40 mm diameter glass cover slip (Warner Instruments, 64-1500) at 1800 rpm to achieve a film thickness of 100 µm. A clear 50 µm thick PDMS layer is spin-coated above the carbon black layer to prevent any potential interactions between PCR reagents in the channel and the carbon black. The microfluidic channel, formed using standard photolithography technique, is plasma bonded to the PDMS above the absorber to enclose the channel. The microfluidic piece is then placed with the top section containing the mask and thermocouples. At this point, the chip is 5 mm thick and 40 mm in diameter. A final 10 mm thick PDMS ring is wrapped around the chip, securing it to the bench top platform and also providing additional insulation. Because these three pieces are all separate, the microfluidic section is easily replaced after each test.

To make the microfluidic channel, SU-8 2075 photoresist (Microchem) is spun on a silicon wafer at 2200 rpm for 30 s to obtain a 100 µm thick film. The SU-8 is then patterned through a chrome photomask (designed in L-Edit, written with the Heidelberg Mask Writer DWL2000) using an ABM Contact Aligner. Uncured SU-8 is removed using SU-8 developer. PDMS is poured over the SU-8 master to a thickness of 3 mm and cured at 80° C. for 2 h. The channel cross section is 100 µm×100 µm and is 1.2 m in length. As a fluid element passes through the channel, it first encounters an initialization zone near 95° C. at the center of the chip of approximately 30 mm in length. It then passes through 35 cycles of the denaturation, annealing and extension zones. Each cycle corresponds to a 32 mm long channel section, which radially spans 10° of space, adding up to 350°. The last 10° is dedicated to a final extension step before the fluid exits.

EXAMPLE 4

According to one embodiment, the microcontroller includes an Arduino Micro board base (Nexuscyber Electronics, ATmega32u4) and three thermocouple breakout amplifiers (Adafruit Industries, MAX31855K) which are each connected with a K-type thermocouple from the chip. To reduce the noise, a 0.01 µf capacitor (AllElectronics Corporation, 103D50) is added across each thermocouple lead. Among the 8 pins of the breakout amplifiers, T+ and T− are used to detect slight changes in voltage between thermocouple leads, while the rest process the reading from the thermocouple and transmit the data through a serial interface. The Arduino Micro reads the serial data from the amplifiers and output it to the smartphone. The Android app is developed in Eclipse with the plug-in Android Development Tools (ADT) and Android SDK. Coding with Arduino 1.0.5 is required for serial data transmission between the MAX31855K amplifier and the Arduino Micro.

For smartphone fluorescent detection, a PDMS chip containing 4 chambers was designed to each hold 20 µL volumes of the samples. A cylindrical lens 2 mm in diameter was molded in the PDMS in front of each chamber to focus the incident light. A 3.4 W blue LED (Sparkfun Electronics, COM-08860) was used as the light source. A blue filter (Thorlabs, FGB25) was placed in front of the LED to reduce light at undesired wavelengths. A green filter (Thorlabs FGV9) is placed above the PDMS chip, perpendicular to the direction that the LED excites the samples. An image of the excited samples is taken in the dark through the green filter. The app then plots the fluorescent signal intensity across each sample, resulting in high peaks for the KSHV+ samples and low peaks for the KSHV− sample and the negative control.

EXAMPLE 5

To demonstrate solar thermal PCR in the range of typical KSHV DNA counts expected from a punch biopsy, plasmid samples were amplified with starting DNA concentrations ranging from $10^8$ to 10 copies/μL, shown in FIG. 7. A 164 bp segment of the KSHV gene vCyclin was selected as the target because the sequence is unique and conserved among different strains. Bands appeared for all samples when analyzed by gel electrophoresis. PCR dependence on flow rate was also analyzed to determine the fastest speed with which a test can be performed. Typically, the reaction speed is constrained by the extension step. The conventional extension rate of Taq polymerase is 60-100 nucleotides/s at 72° C. Thus, 3 s should be sufficient for full extension of a 164 bp product. The design of the channel suggests that a minimum reaction time of 10 s/cycle is required. Experiments were performed with cycling times ranging from 5 s/cycle to 50 s/cycle, which for the 10 μL sample size corresponded to total reaction times of 6 min to 55 min (FIG. 7). Intensity values were normalized by a reference sample that was run in a conventional thermal cycler for 2 h. Band intensity increased significantly near 20 s/cycle, showing that a 10 μL sample can be amplified and extracted within 30 min.

EXAMPLE 6

After having developed the solar thermal PCR system to work under a range of conditions, it was then demonstrated that PCR can be performed for approximately 12 h each day during the summer months. FIG. 8A shows on-chip temperatures in July from 7 AM to 7 PM. By setting the lens-to-chip distance at 85 mm, the necessary temperatures were usually obtained within 3 min, while longer times were required in the morning when ambient temperature is cooler and sunlight is less intense. For the data presented, temperatures varied from 25° C. in the morning to 32° C. in the early afternoon. FIG. 8B shows that as the day warmed in the morning, the denaturation temperature decreased while the extension and annealing temperatures increased. The trends were reversed in the late afternoon as ambient temperature cooled. The on-chip thermal fluctuations did not noticeably inhibit amplification, demonstrating that PCR can be successfully performed for most of the daylight hours.

EXAMPLE 7

In the field, clouds can manifest in a number of forms that affect PCR efficiency. To examine the influence of clouding in a controlled manner, a solar simulator was designed using a 100 W LED. Optical lenses were set up to collimate the light and create similar temperatures on the chip. To mimic clouding, the light was blocked 5 min after the PCR process began for a duration that ranged from 15 s to 4 min. The resulting thermal profiles are shown in FIG. 9a. The DNA melting temperature of 86° C., calculated using the nearest neighbor method, served as a threshold for the denaturation step to define the percent of time that the sample spends below acceptable conditions for PCR. These were calculated to range from 2% (15 s light obstruction) to 33% (4 min light obstruction) for tests with a total flow-through time of 27 min. The band intensities shown in FIGS. 9b and 9c suggest an exponential decay as the duration of simulated clouding increases.

EXAMPLE 8

To demonstrate compatibility with solid tissue processing and low-power detection, human skin biopsies were analyzed both with and without KS involvement by combining solar thermal PCR with single-tube HotSHOT DNA extraction and smartphone fluorescence detection. FIG. 10a shows a smartphone-powered blue LED incident on a PDMS chip containing 4 samples. Each sample includes SYBR Green dye, which preferentially binds to double-stranded DNA and emits green light when excited by blue light. The chip shown in FIG. 10a, b contains two KSHV+ samples (1, 2), a KSHV− sample (3), and a negative control (NC). Samples 1-3 were mixed with a dry room-temperature PCR reagent kit and amplified by solar thermal PCR, while NC was mixed with a conventional refrigerated PCR reagent kit and run in a thermal cycler. An app compared the average fluorescent signals of the three test samples to NC, providing the user with the correct diagnosis for each (FIG. 10c). In practice, an intensity threshold could be determined based on multiple tests to provide on-site diagnosis. By tracking the battery depletion of the smartphone over a number of PCR tests, a power consumption of 80 mW was calculated, which is two orders of magnitude lower than commercial products. For the 10 Wh smartphone battery used, this would enable a battery life of 120 h, compared to 27 h for the academic state-of-the-art and 2 h for commercial devices.

EXAMPLE 9

PCR sample preparation. A 70 μL volume of DI water containing 4.3% w/v polyvinylpyrrolidone (PVP) (Sigma-Aldrich, 437190) was mixed with PCR reagents (Invitrogen, N8010055) including 10 μL of 10× PCR buffer, 0.2-mM dNTPs, 10 Units/100 μL of Taq polymerase, 1 μM of forward and reverse primers and 1 μL of target DNA. PVP was used here to inhibit Taq adsorption onto the PDMS surface.

Solar thermal PCR procedure. The channel was first passivated with a 7.5 mg/mL bovine serum albumin (Sigma-Aldrich, A7888) solution for 2 h to further inhibit Taq adsorption, and flushed with DI water at 1 μL/min for 30 min to remove unbound particles. During the test, a 20 μL paraffin oil plug (VWR, BDH3338) was pumped through the chip, followed by a 10 μL sample, and then another oil plug. The two plugs prevent sample evaporation caused by heating. Unless specified, samples contained an initial DNA concentration of $10^5$ copies/μL and tests were conducted with a syringe pump (New Era, NE-1000) set at 1 μL/min. Due to absorption of the oil into the PDMS, the actual flow rate was calculated to be 0.8 μL/min based on the time the samples took to go from the inlet to the outlet.

Sample preparation for smartphone fluorescence detection. The negative control included 25 μL of Power SYBR Green PCR master mix (Invitrogen, 4368577) combined with 15 μL of DI water, 1 μM of forward and reverse primers and 10 μL of KSHV− solution. Tests 1-3 used High Yield PCR EcoDry Premix (Clontech, 639278) mixed with 15 μL of 5% w/v PVP in DI water, 10 Units/100 μL of Taq polymerase, 1 μM of forward and reverse primers, and 10 μL of KSHV+ biopsy solution (samples 1 and 2) or KSHV− solution (sample 3). After amplification, 10 μL of the products were added to 10 μL SYBR Green solution and injected into the chambers.

According to aspects of the invention, the device can be utilized in, for example, point-of-care diagnostics, particularly in low resource environments where electricity is unreliable. While embodiments are provided in which the device provides simply the DNA amplification process which, similar to the Palm PCR can be a self-contained product, according to other embodiments the device and method can be integrated with processing and detection steps to create a low-power fully integrated assay. For example, such a system could include an on-chip lysing step prior to PCR amplification, and/or a gold nanoparticle-based detection step after PCR amplification. The technologies behind these processes are described in PCT Application No. PCT/US13/26127 entitled "Apparatus, Methods, and Applications for Point of Care Multiplexed Diagnostics," the entire contents of which are hereby incorporated by reference in their entirety. For example, gold nanoparticles can be designed to aggregate in the presence of a specific strand of DNA. This aggregation causes a color change in the solution. Similarly, a smartphone application can be used to take images of the solution, analyze the color change and provide in-field test results. In addition to infectious disease applications, solar-powered PCR could, in principle, be applied to a number of other areas where traditional PCR has found utility, but is not frequently used in limited resource settings due to environmental constraints. For example, in the field of forensics, it could be used to recover information from small or degraded samples directly from a crime scene.

Although the present invention has been described in connection with a preferred embodiment, it should be understood that modifications, alterations, and additions can be made to the invention without departing from the scope of the invention as defined by the claims.

What is claimed is:

1. A solar-thermal microfluidic polymerase chain reaction (PCR) device, the PCR device comprising:
    a microfluidic chip including at least one PCR region;
    a light energy absorption layer disposed adjacent to the microfluidic chip;
    a solar energy concentrator adapted to produce a plurality of spatially modulated temperature profiles on the microfluidic chip, the plurality of spatially modulated temperature profiles adapted to facilitate PCR within said PCR region; and
    a photomask disposed between said solar energy concentrator and said microfluidic chip.

2. The device of claim 1, further comprising a sensor coupled to said microfluidic chip.

3. The device of claim 2, wherein said sensor is a thermometer.

4. The device of claim 2, further comprising a user interface coupled to the sensor.

5. The device of claim 1, wherein the distance between the solar energy concentrator and the microfluidic device is adjustable.

6. The device of claim 1, wherein the distance between said photomask and said solar energy concentrator is adjustable.

7. The device of claim 6, wherein the opacity of the photomask is adjustable.

8. The device of claim 1, wherein said photomask comprises a plurality of nested aluminum rings.

9. The device of claim 1, wherein the plurality of spatially modulated temperature profiles comprises a first, denaturation temperature profile, a second, annealing temperature profile, and a third, elongation temperature profile.

10. The device of claim 9, wherein said microfluidic chip is configured to allow said sample to pass through said three temperature profiles in a time ratio of approximately 4:4:9.

11. A system for solar-thermal microfluidic polymerase chain reaction (PCR) amplification of nucleic acid, the system comprising:
    a sample comprising nucleic acid;
    a solar-thermal microfluidic PCR device comprising: (i) a microfluidic chip comprising a microfluidic chamber adapted to facilitate PCR of said sample; (ii) a solar energy absorption layer disposed adjacent to the microfluidic chip; (iii) a solar energy concentrator adapted to produce a plurality of spatially modulated temperature profiles on the microfluidic chip, the plurality of spatially modulated temperature profiles adapted to facilitate PCR within a PCR region; and (iv) a photomask disposed between said solar energy concentrator and said microfluidic chip.

12. The system of claim 11, wherein said solar-thermal microfluidic PCR device further comprises a thermometer.

13. The system of claim 11, wherein the opacity of the photomask is adjustable.

14. The system of claim 11, wherein said photomask comprises a plurality of nested aluminum rings.

15. The system of claim 11, wherein the plurality of spatially modulated temperature profiles comprises a first, denaturation temperature profile, a second, annealing temperature profile, and a third, elongation temperature profile.

16. A method for facilitating microfluidic polymerase chain reaction (PCR) amplification of nucleic acid, the method comprising the steps of:
    providing a sample comprising nucleic acid;
    providing a solar-thermal microfluidic PCR device comprising: (i) a microfluidic chip comprising a microfluidic chamber adapted to facilitate PCR of said sample; (ii) a light energy absorption layer disposed adjacent to the microfluidic chip; (iii) a solar energy concentrator adapted to produce a plurality of spatially modulated temperature profiles on the microfluidic chip, the plurality of spatially modulated temperature profiles adapted to facilitate PCR within said PCR region; and (iv) a photomask disposed between said solar energy concentrator and said microfluidic chip;
    applying said sample to said microfluidic chamber; and
    performing PCR using said solar-thermal microfluidic PCR device.

17. The method of claim 16, further comprising the step of detecting a temperature of said solar-thermal microfluidic PCR device.

18. The method of claim 16, further comprising the step of adjusting the distance between the solar energy concentrator and the microfluidic device.

19. The method of claim 16, further comprising the step of adjusting the opacity of the photomask.

20. The method of claim 16, further comprising the step of monitoring one or more of the plurality of spatially modulated temperature profiles.

* * * * *